United States Patent
Nilsson et al.

(10) Patent No.: US 9,220,454 B2
(45) Date of Patent: Dec. 29, 2015

(54) DEVICE AND METHOD FOR DETECTING DROWSINESS USING EYELID MOVEMENT

(75) Inventors: Benny Nilsson, Alingsas (SE); Erik Rosen, Alingsas (SE)

(73) Assignee: AUTOLIV DEVELOPMENT AB, Vargarda (SE)

( * ) Notice: Subject to any disclaimer, the term of this patent is extended or adjusted under 35 U.S.C. 154(b) by 0 days.

(21) Appl. No.: 14/419,318

(22) PCT Filed: Aug. 20, 2012

(86) PCT No.: PCT/SE2012/050889
§ 371 (c)(1),
(2), (4) Date: Feb. 3, 2015

(87) PCT Pub. No.: WO2014/031042
PCT Pub. Date: Feb. 27, 2014

(65) Prior Publication Data
US 2015/0208977 A1  Jul. 30, 2015

(51) Int. Cl.
*G06K 9/00* (2006.01)
*A61B 5/18* (2006.01)
*B60K 28/06* (2006.01)
(Continued)

(52) U.S. Cl.
CPC ............. *A61B 5/18* (2013.01); *A61B 5/1103* (2013.01); *B60K 28/06* (2013.01); *B60K 28/066* (2013.01); *G06K 9/00845* (2013.01); *G06T 7/2033* (2013.01); *G08B 21/06* (2013.01); *B60W 2540/26* (2013.01); *G06T 2207/10016* (2013.01); *G06T 2207/30201* (2013.01)

(58) Field of Classification Search
USPC ......... 382/100, 103–107, 117, 155, 162, 168, 382/173, 181, 199, 209, 219, 232, 254, 274, 382/276, 286–291, 305, 312; 340/576, 575
See application file for complete search history.

(56) References Cited

U.S. PATENT DOCUMENTS

| | | | | |
|---|---|---|---|---|
| 6,243,015 | B1 * | 6/2001 | Yeo ........................ | G08B 21/06 340/575 |
| 7,791,491 | B2 * | 9/2010 | Johns ...................... | A61B 5/18 340/575 |

(Continued)

FOREIGN PATENT DOCUMENTS

| | | |
|---|---|---|
| EP | 2 111 796 A1 | 10/2009 |
| EP | 2 237 237 A1 | 10/2010 |

(Continued)

OTHER PUBLICATIONS

PCT International Search Report—May 13, 2013.

*Primary Examiner* — Seyed Azarian
(74) *Attorney, Agent, or Firm* — Brinks Gilson & Lione

(57) ABSTRACT

A drowsiness detection device and method for a person (4), having a digital camera device (2) and a control unit (5). The digital camera device (2) includes a video processor (6). The digital camera device (2) is arranged to detect the eyes (3) of the person (4) in a series of images. The video processor (6) is arranged to detect eyelid movements in the images and convert images of the eyelid movements to an electric signal (s(t)) which is transferred to the control unit (5) The control unit (5) is arranged to fit a modeled signal (y(t)) against the electric signal (s(t)) and to determine whether the modeled signal (y(t)) constitutes an eyelid blink. The control unit (5) uses a number of modeled signals (y(t)) determined to constitute an eyelid blink to determine whether the level of alertness has fallen below a certain threshold.

7 Claims, 5 Drawing Sheets

(51) Int. Cl.
  *G08B 21/06* (2006.01)
  *A61B 5/11* (2006.01)
  *G06T 7/20* (2006.01)
  *G08B 23/00* (2006.01)

(56) References Cited

U.S. PATENT DOCUMENTS

| | | | |
|---|---|---|---|
| 2006/0077064 A1 | 4/2006 | Baura | |
| 2008/0150734 A1* | 6/2008 | Johns | A61B 5/18 340/575 |
| 2009/0040054 A1* | 2/2009 | Wang | B60W 30/095 340/576 |
| 2009/0123031 A1* | 5/2009 | Smith | A61B 5/18 382/104 |
| 2010/0245093 A1* | 9/2010 | Kobetski | A61B 5/18 340/576 |

FOREIGN PATENT DOCUMENTS

| | | |
|---|---|---|
| EP | 2 351 524 A1 | 8/2011 |
| YU | WO 02/50792 A1 | 6/2002 |

* cited by examiner

DEVICE AND METHOD FOR DETECTING DROWSINESS USING EYELID MOVEMENT

CROSS REFERENCE TO RELATED APPLICATIONS

This application claims priority to PCT International Patent Application No. PCT/SE2012/050889, filed on Aug. 20, 2012.

FIELD OF THE INVENTION

The present invention relates to a method for detecting the level of alertness of a vehicle driver. The method comprises the steps: detecting eyelid movements of the vehicle driver, creating an electric signal that represents the detected eyelid movements, analyzing the electric signal and determining, based on the analysis results, whether the level of alertness of the vehicle driver falls below a certain threshold.

The present invention also relates to a vehicle driver drowsiness detection device, the device comprising a digital camera device and a control unit. The digital camera device in turn comprises a video processor, where the digital camera device is arranged to detect the eyes of a person driving a vehicle in a series of images. The video processor is arranged to detect eyelid movements in the images and convert images of the eyelid movements to an electric signal which is transferred to the control unit.

BACKGROUND OF THE INVENTION

Detection of vehicle driver drowsiness is desirable since drowsiness impairs the ability of a driver of vehicles such as motor vehicles, trains, aircraft and boats. It may also be desirable to detect drowsiness for operators of industrial equipment and the like. Drowsiness may for example be due to not enough sleep or the use of drugs.

A problem regarding drowsiness is that, generally, persons do not detect their own drowsiness when it appears due to the nature of drowsiness. It is thus difficult for a person to predict when the level of drowsiness will become dangerous.

Today, many devices and methods for measuring eyelid movements in order to detect drowsiness of a vehicle driver are known, and in most cases a digital camera captures images of at least one of the vehicle driver's eyes. These images are then processed in different ways in order to detect drowsiness. U.S. Pat. No. 7,791,491 discloses usage of amplitude/velocity ratio of eyelid opening and closing to measure drowsiness. U.S. Pat. No. 6,243,015 describes how an eye's vertical width is determined and compared with a threshold value.

However, the previously known devices and methods for measuring eyelid movements suffer from erroneous alerts that are due to inferior eyelid detection and image processing, which for example is sensitivity to signal noise.

There is thus a need for a device and a method for measuring eyelid movements in order to detect drowsiness of a person, which device and method are more robust than previously known equipment of this kind, and where the risk of false alerts is reduced.

INTRODUCTORY DESCRIPTION OF THE INVENTION

The above referenced object is achieved in accordance with the present invention by means of a method for detecting the level of alertness of a person, the method comprising the steps: detecting eyelid movements of the person, creating an electric signal that represents the detected eyelid movements, analyzing the electric signal and determining, based on the analysis results, whether the level of alertness of the person falls below a certain threshold. Furthermore, the step of analyzing the electric signal comprises fitting a modeled signal against the electric signal and determining whether the modeled signal constitutes an eyelid blink. The step of determining whether the level of alertness of the person falls below a certain threshold uses a number of modeled signals that each has been determined to constitute an eyelid blink.

The above referenced object is also achieved by means of a person drowsiness detection device, the drowsiness detection device comprising a digital camera device and a control unit. The digital camera device in turn comprises a video processor, where the digital camera device is arranged to detect the eyes of a person in a series of images. The video processor is arranged to detect eyelid movements in said images and convert images of the eyelid movements to an electric signal which is transferred to the control unit. The control unit is arranged to fit a modeled signal against the electric signal and to determine whether the modeled signal constitutes an eyelid blink. The control unit is further arranged to use a number of modeled signals that each has been determined to constitute an eyelid blink in order to determine whether the level of alertness of the person has fallen below a certain threshold.

According to an example, each modeled signal is defined as $$y(t) = \begin{cases} k_1 \cdot \log(t_2 - t) + m_1 & \text{for } t_1 \leq t < t_2 \\ m_2 & \text{for } t_2 \leq t < t_3 \\ k_3 \cdot \log(t - t_3) + m_3 & \text{for } t_3 < t \leq t_4 \end{cases}$$

where $k_1$, $k_3$, $m_1$, $m_2$ and $m_3$ are constants that are defined for each eyelid blink and the times $t_1$, $t_2$, $t_3$, $t_4$ define time intervals of the modeled signal.

According to another example, in order to fit a modeled signal against the electric signal an error $\epsilon$ is calculated according to $$\varepsilon = \frac{1}{N} \cdot \sum_{i=sample(t_1)}^{sample(t_4)} |s(i) - y(i)|$$

such that the times $t_1$, $t_2$, $t_3$, $t_4$ defining the time intervals as well as the constant $m_2$ are varied to minimize the error $\epsilon$. The other constants $k_1$, $k_3$, $m_1$ and $m_3$ are estimated by using regression.

Other examples are disclosed in this description of the invention.

A number of advantages are obtained by means of the present invention. Mainly, measuring eyelid movements may be performed in a more robust way, where the risk of false alerts is reduced.

BRIEF DESCRIPTION OF THE DRAWINGS

The present invention will now be described more in detail with reference to the appended drawings, where.

DETAILED DESCRIPTION

Figure 1:
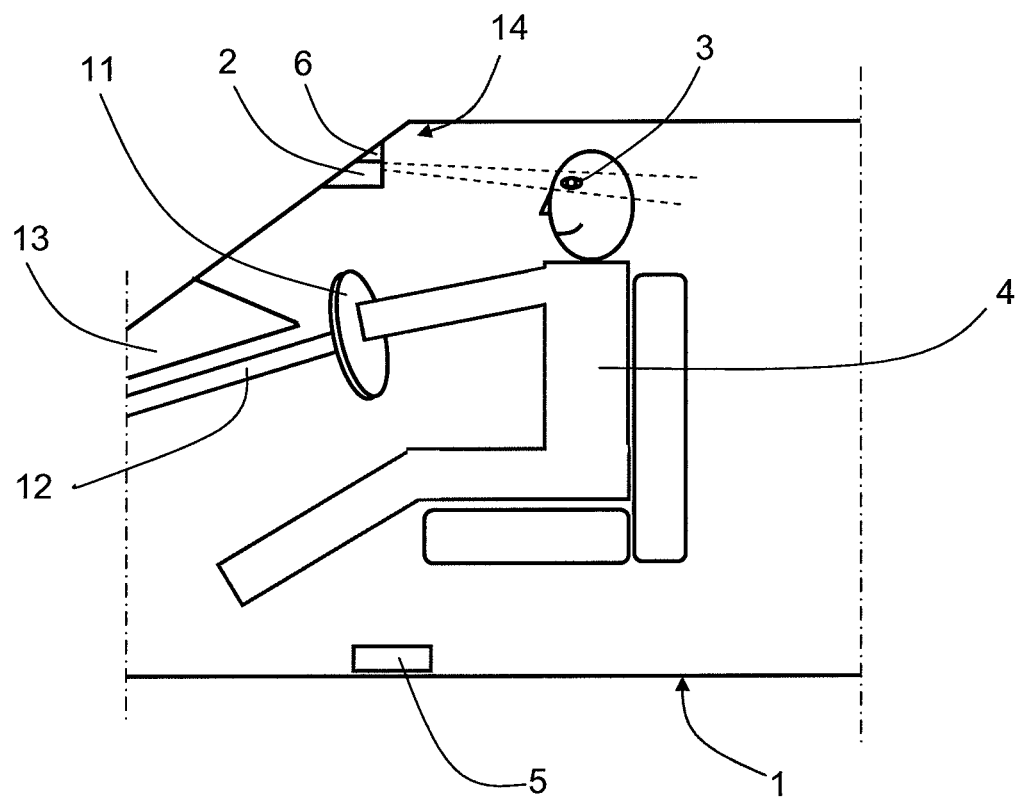
FIG. 1 shows a schematic cut-open side view of a vehicle with a digital camera device.

FIG. 1 schematically shows a cut-open part of a vehicle 1, where the vehicle 1 includes a digital camera device 2. The digital camera device 2, which may include a light source (not shown), is arranged for capturing images of the eyes 3 of a person 4 driving the vehicle 1 and transferring these images to a control unit 5. In particular, the eyelid movements are of interest, since they are used to determine whether the person 4 driving the vehicle 1 is becoming drowsy or not.

More in detail, by way of example, the digital camera device 2 may operate at a frame rate of 60 Hz. Other frame rates, such as for example 40 Hz, are also conceivable. The digital camera device 2 is arranged to detect the eyes 3 of the person 4 driving the vehicle 1 in a series of images. A video processor 6 which may be integrated in the digital camera device 2 is arranged to detect eyelid movements in these images and convert the images of the eyelid movements to a signal. This signal is then transferred to the control unit 5, where the signal is filtered in order to reduce noise.

Figure 2:
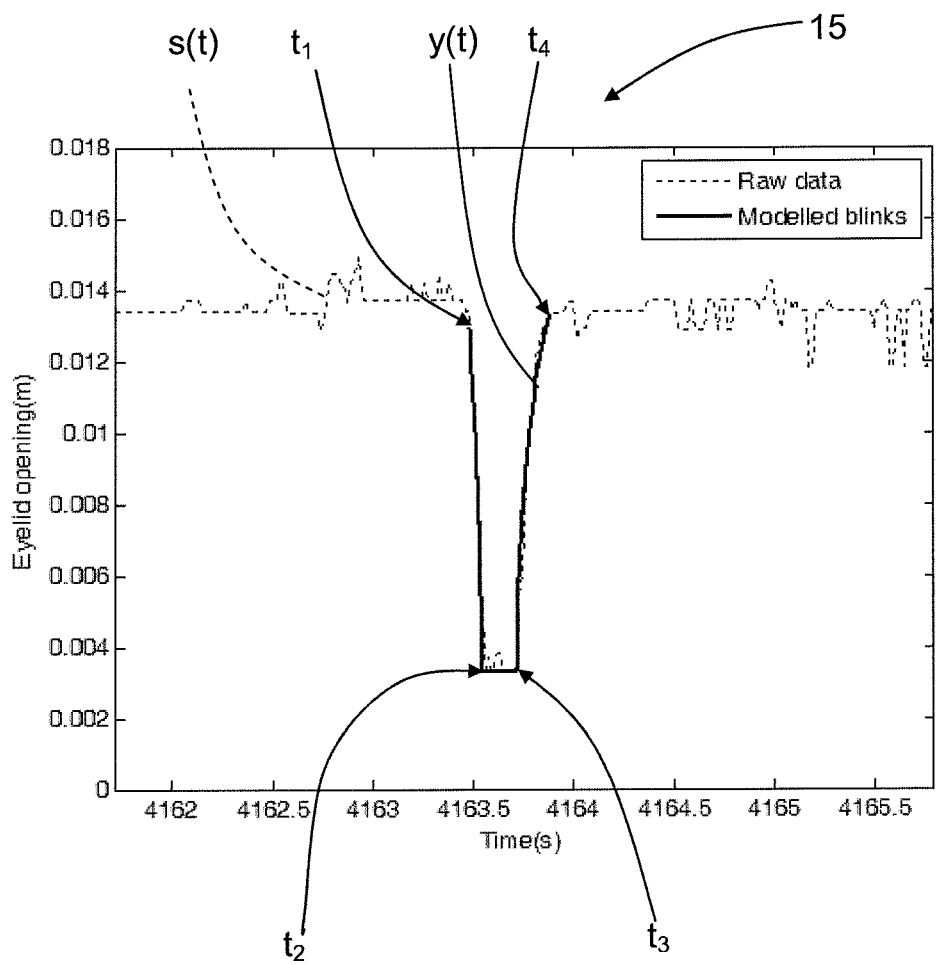
FIG. 2 shows a first graph of a filtered signal that corresponds to eyelid movements.
Figure 3:
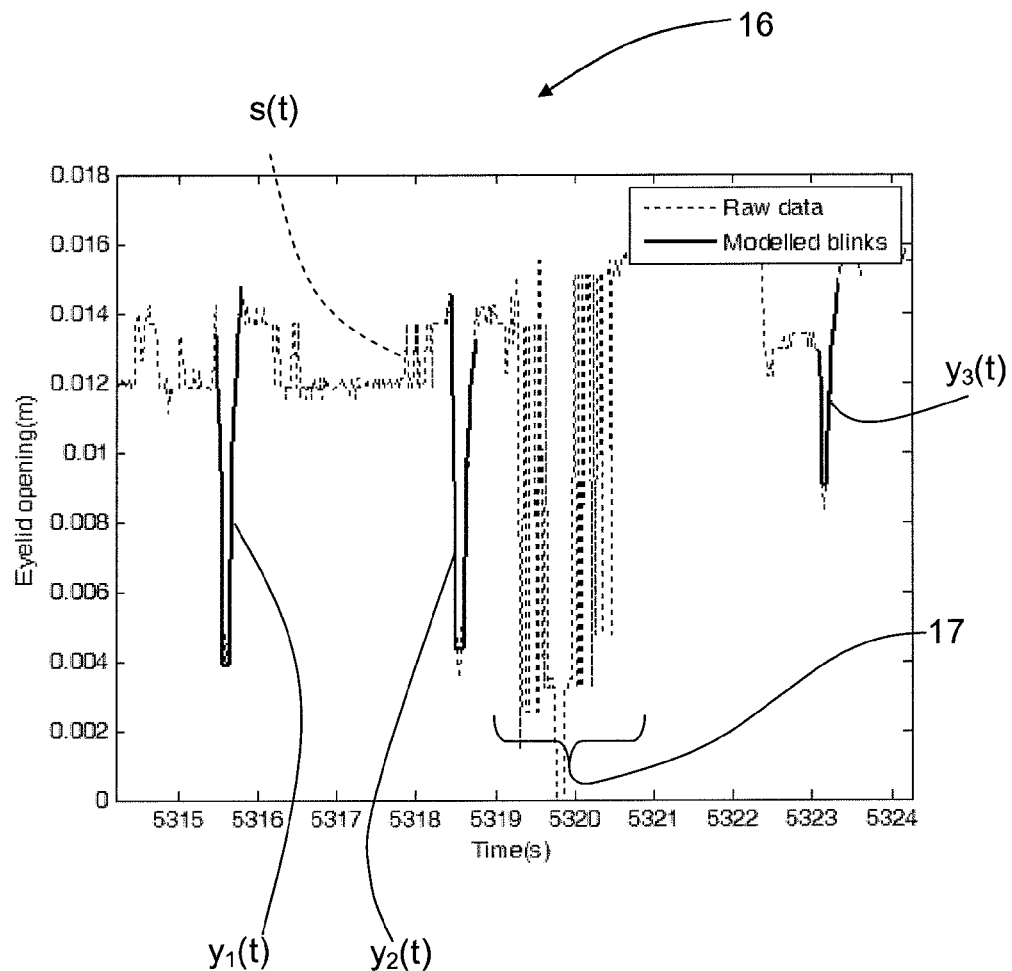
FIG. 3 shows a second graph of a filtered signal that corresponds to eyelid movements.

FIG. 2 shows a first graph 15 of the filtered signal s(t) that corresponds to eyelid movements, indicated with dashed lines and marked as "raw data" in FIG. 3. The x-axis shows time in seconds and the y-axis shows the eyelid opening in meters. Furthermore, a graph showing the fitted modeled signal y(t) that has been created to be compared with the filtered signal s(t) is indicated by a bold solid line and is marked as "modeled blinks" in FIG. 3.

The modeled signal y(t) is in this example defined as:

$$y(t) = \begin{cases} k_1 \cdot \log(t_2 - t) + m_1 & \text{for } t_1 \leq t < t_2 \\ m_2 & \text{for } t_2 \leq t < t_3 \\ k_3 \cdot \log(t - t_3) + m_3 & \text{for } t_3 < t \leq t_4 \end{cases} \quad (1)$$

where $k_1, k_3, m_1, m_2$ and $m_3$ are constants that are defined for each blink. The first time interval $t_1 \leq t < t_2$ lies between a first flank value at a first time $t_1$ and a first flank minimum value at a second time $t_2$ the second time interval $t_2 \leq t <_3$ lies between the first flank minimum value and a second flank minimum value at a third time $t_3$, and the third time interval $t_3 < t \leq t_4$ lies between the second flank minimum value and a second flank value at a fourth time $t_4$, as illustrated in FIG. 2. The modeled signal y(t) is thus considered as a constant $m_2$ between the flank minimum values. The modeled signal y(t) is furthermore only defined between the first time $t_1$ and the second time $t_4$ of the second flank value, each time $t_1, t_2, t_3, t_4$, being positioned at a discontinuity of the modeled signal y(t) since it changes character at each such time.

En error function to find an error $\epsilon$ is defined as:

$$\varepsilon = \frac{1}{N} \cdot \sum_{i=sample(t_1)}^{sample(t_4)} |s(i) - y(i)| \quad (2)$$

where N is the number of samples. The error $\epsilon$ is thus defined as a mean absolute error between the filtered signal s(t) and the modeled signal y(t), where the times $t_1, t_2, t_3, t_4$ defining the intervals as well as the constant $m_2$ are varied to minimize the error $\epsilon$. The other constants $k_1, k_3, m_1$ and $m_3$ are estimated by means of regression.

The modeled signal y(t) is repeatedly fitted against the electric signal s(t) such that a number of modeled signals y(t) are acquired. For each acquired modeled signal y(t) it is determined whether it represents an eyelid blink, such that a number of modeled signals y(t) where each represents an eyelid blink are acquired. Determining whether a modeled signal y(t) represents an eyelid blink or not may be performed by using an error threshold and the plausibility of opening and closing parameters. If any of the conditions set up for an eyelid blink is not met, the modeled signal y(t) tested is not considered to represent an eyelid blink; otherwise it is considered to represent an eyelid blink.

The modeled signals y(t) which represent an eyelid blink are then used for determining whether the level of alertness of the vehicle driver falls below a certain threshold. The threshold may be set in many ways and at different levels, which is easily conceivable for the skilled person and will not be further discussed here.

FIG. 3 shows a second graph 16, being of the same kind as the first graph 15, where the filtered signal s(t) is shown to have a part with disturbances 17. A first modeled signal $y_1(t)$, a second modeled signal $y_2(t)$ and a third modeled signal $y_3(t)$ have been considered to constitute eyelid blinks. By means of the present invention, it has been possible to discard the part of the filtered signal s(t) with disturbances 17, since it has not been possible to fit a modeled signal to the filtered signal s(t) at that part where the error c is below a predetermined threshold.

Figure 4:
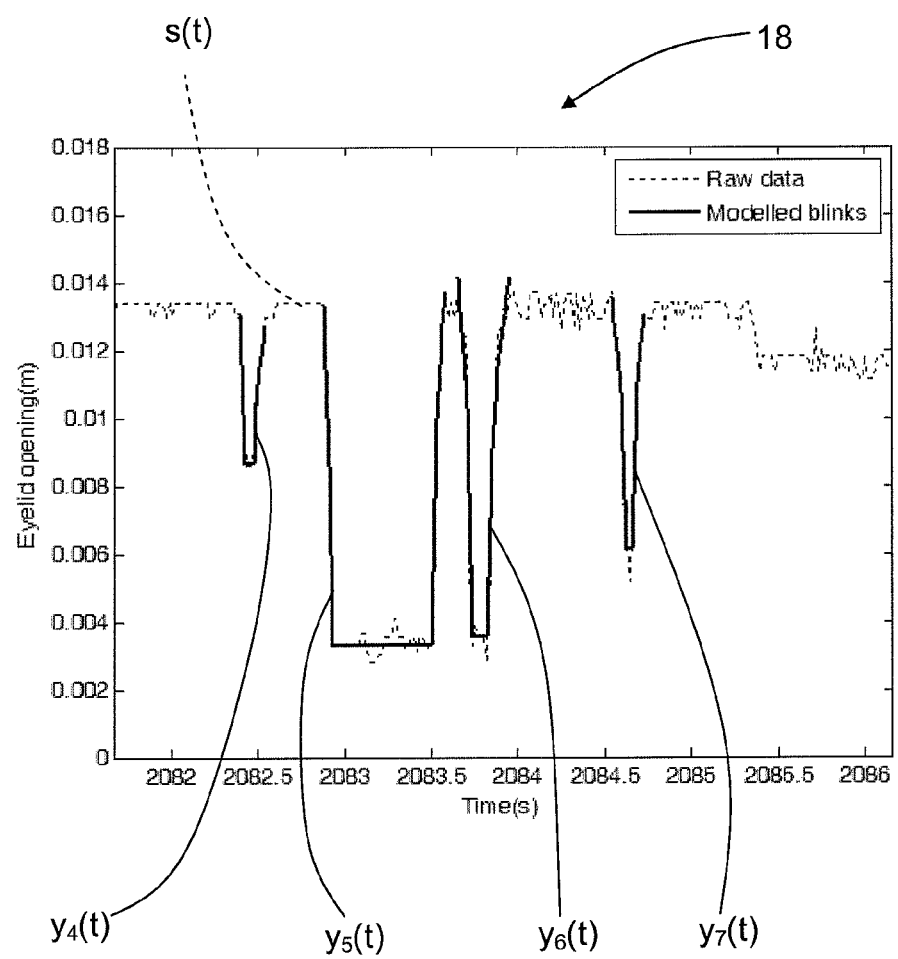
FIG. 4 shows a third graph of a filtered signal that corresponds to eyelid movements.

FIG. 4 shows a third graph 18, being of the same kind as the first two graphs 15, 16. FIG. 4 shows how a fourth modeled signal $y_4(t)$, a fifth modeled signal $y_5(t)$, a sixth modeled signal $y_6(t)$ and a seventh modeled signal $y_7(t)$ have been considered to constitute eyelid blinks, where the fifth modeled signal $y_5(t)$ corresponds to an eyelid blink that extends over a clearly longer period of time then the other modeled signals $y_4(t), y_6(t), y_7(t)$.

These graphs 16, 18 show examples of the versatility and robustness of the present invention.

Figure 5:
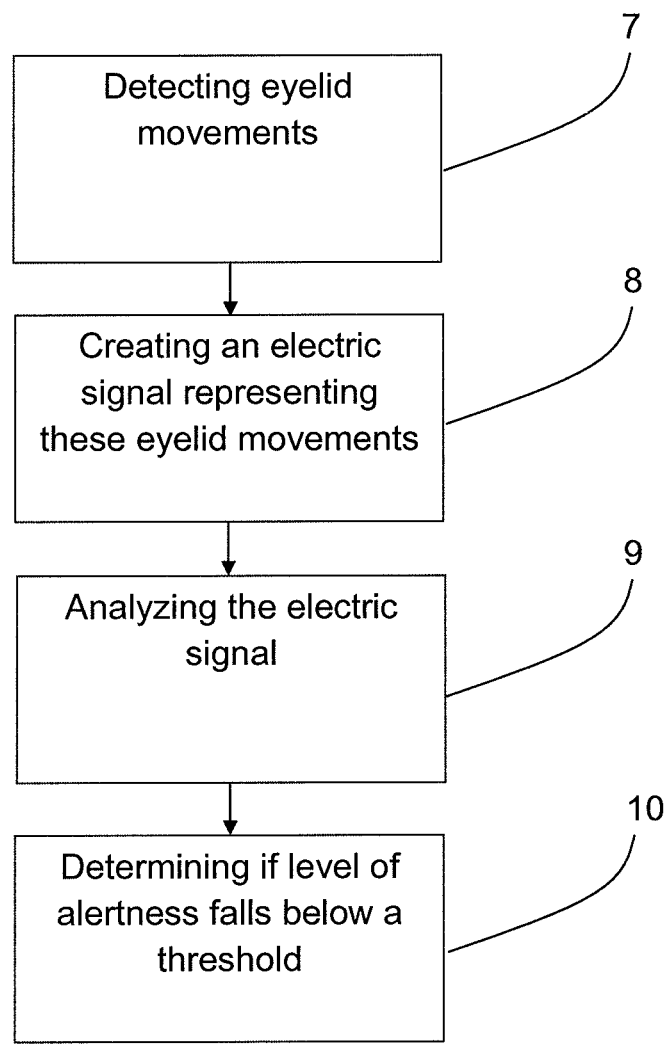
FIG. 5 shows a flowchart for a method according to the present invention.

With reference to FIG. 5, the present invention relates to a method for detecting the level of alertness of a vehicle driver, the method comprising the steps:

7: detecting eyelid movements of the vehicle driver;

8: creating an electric signal that represents the detected eyelid movements;

9: analyzing the electric signal; and

10: determining, based on the analysis results, whether the level of alertness of the vehicle driver falls below a certain threshold.

In the steps above, analyzing the electric signal s(t) comprises fitting a modeled signal y(t) against the electric signal s(t) and determining whether the modeled signal y(t) constitutes an eyelid blink. Furthermore, the step of determining whether the level of alertness of the vehicle driver falls below a certain threshold uses a number of modeled signals y(t) that each has been determined to constitute an eyelid blink.

The present invention is not limited to the examples above, but may vary freely within the scope of the appended claims. For example, it is not necessary to filter the signal, and in that case the unfiltered signal constitutes the signal s(t) against which the modeled signal y(t) is fitted.

The signals y(t), s(t) are in the form of electric signals.

With reference to FIG. 1, the digital camera device 6 may be of any suitable kind, and may be placed in any suitable position in the vehicle 1, for example at the steering wheel 11 rim or spokes, at the steering column 12, at the dashboard 13 or in the ceiling 14. Other examples are airbag covers.

Generally, the present invention is not only applicable for a vehicle driver 4, but for any person where it is suitable to detect drowsiness. Examples are operators of industrial equipment and/or control equipment, such as an operator at a nuclear power plant or at a industrial process.

The digital camera device 2 is arranged to detect at least one eye 3 of the person 4 in a series of images, the eyelid movements being analyzed for either one eye or two eyes depending on how many eyes that are detected by the digital camera device 2. It is also conceivable that two eyes are detected by the digital camera device 2, but the eyelid movements are analyzed for only one eye.

While the above description constitutes the preferred embodiment of the present invention, it will be appreciated that the invention is susceptible to modification, variation and change without departing from the proper scope and fair meaning of the accompanying claims.

The invention claimed is:

1. A method for detecting the level of alertness of a person, the method comprising the steps:
   detecting eyelid movements of the person by a camera in communication with a control unit;
   creating an electric signal (s(t)) from the camera that represents the detected eyelid movements;
   analyzing the electric signal (s(t)) by the control unit by fitting a modeled signal (y(t)) against the electric signal (s(t)), the modeled signal (y(t)) is defined as:

$$y(t) = \begin{cases} k_1 \cdot \log(t_2 - t) + m_1 & \text{for } t_1 \leq t < t_2 \\ m_2 & \text{for } t_2 \leq t < t_3 \\ k_3 \cdot \log(t - t_3) + m_3 & \text{for } t_3 < t \leq t_4 \end{cases}$$

where $k_1$, $k_3$, $m_1$, $m_2$ and $m_3$ are constants that are defined for each eyelid blink and the times $t_1$, $t_2$, $t_3$, $t_4$ define time intervals of the modeled signal (y(t));
   determining by the control unit whether the modeled signal (y(t)) constitutes an eyelid blink; and
   determining by the control unit, based on the analyzing step, whether the level of alertness of the person falls below a certain threshold using a plurality of the modeled signals (y(t)) when each of the modeled signals has been determined to constitute the eyelid blink.

2. A method according to claim 1, further comprising that the control unit fitting a modeled signal (y(t)) against the electric signal (s(t)) comprises the steps of:

calculating an error ε according to $$\varepsilon = \frac{1}{N} \cdot \sum_{i=sample(t_1)}^{sample(t_4)} |s(i) - y(i)|$$

such that the times $t_1$, $t_2$, $t_3$, $t_4$ defining the time intervals and the constant $m_2$ are varied to minimize the error ε; and estimating the other constants $k_1$, $k_3$, $m_1$ and $m_3$ using regression.

3. A method according to claim 1 further comprising that the electric signal (s(t)) is filtered by the control unit in order to reduce noise.

4. The method for detecting the level of alertness of the person in accordance with claim 1 further comprising the step of detecting eyelid movements of the person includes capturing a plurality of images of the eyes.

5. The drowsiness detection device for a person in accordance with claim 4 further comprising the digital camera device captures a plurality of the images of the eyes.

6. A drowsiness detection device for a person, the drowsiness detection device comprising a digital camera device and a control unit is configured to fit a modeled signal (y(t)) against an electric signal (s(t)) from the camera device and to determine whether the modeled signal (y(t)) constitutes an eyelid blink, where the control unit further is arranged to use a plurality of the modeled signals (y(t)) that each has been determined to constitute the eyelid blink in order to determine whether the level of alertness of the person has fallen below a certain threshold, the modeled signal (y(t)) is defined as:

$$y(t) = \begin{cases} k_1 \cdot \log(t_2 - t) + m_1 & \text{for } t_1 \leq t < t_2 \\ m_2 & \text{for } t_2 \leq t < t_3 \\ k_3 \cdot \log(t - t_3) + m_3 & \text{for } t_3 < t \leq t_4 \end{cases}$$

where $k_1$, $k_3$, $m_1$, $m_2$ and $m_3$ are constants that are defined for each eyelid blink and the times $t_1$, $t_2$, $t_3$, $t_4$ define time intervals of the modeled signal (y(t)), the digital camera device including a video processor, where the digital camera device is arranged to detect at least one eye of the person in a series of images, and the video processor is arranged to detect eyelid movements in the images and convert images of the eyelid movements to an electric signal (s(t)) which is transferred to the control unit).

7. A drowsiness detection device according to claim 6, further comprising that the control unit is arranged to filter the received electric signal such that the control unit is arranged to fit the modeled signal (y(t)) against the filtered electric signal (s(t)).

* * * * *